United States Patent
Cumbo et al.

(10) Patent No.: US 10,444,138 B2
(45) Date of Patent: Oct. 15, 2019

(54) OPTICAL CELL CONSTRUCTED BY ANODICALLY BONDING A THIN METAL LAYER BETWEEN TWO OPTICALLY CLEAR GLASS WINDOWS

(71) Applicant: Eta Diagnostics, Inc., Albuquerque, NM (US)

(72) Inventors: Michael J Cumbo, Albuquerque, NM (US); Travis A Woods, Albuquerque, NM (US); Steven Wayde Graves, Albuquerque, NM (US); Trevor Turbov, Albuquerque, NM (US)

(73) Assignee: BennuBio, Inc., Albuquerque, NM (US)

( * ) Notice: Subject to any disclaimer, the term of this patent is extended or adjusted under 35 U.S.C. 154(b) by 0 days.

(21) Appl. No.: 15/561,133

(22) PCT Filed: Mar. 25, 2016

(86) PCT No.: PCT/US2016/024306
§ 371 (c)(1),
(2) Date: Sep. 25, 2017

(87) PCT Pub. No.: WO2016/154578
PCT Pub. Date: Sep. 29, 2016

(65) Prior Publication Data
US 2018/0052095 A1    Feb. 22, 2018

Related U.S. Application Data

(60) Provisional application No. 62/138,192, filed on Mar. 25, 2015.

(51) Int. Cl.
| | | |
|---|---|---|
| *G01N 21/01* | (2006.01) | |
| *G01N 21/03* | (2006.01) | |
| *G02B 1/06* | (2006.01) | |
| *G01N 21/05* | (2006.01) | |

(52) U.S. Cl.
CPC ............. *G01N 21/01* (2013.01); *G01N 21/03* (2013.01); *G02B 1/06* (2013.01); *G01N 2021/058* (2013.01)

(58) Field of Classification Search
CPC .. G01N 21/01; G01N 21/03; G01N 2021/058; G02B 1/06
See application file for complete search history.

(56) References Cited

U.S. PATENT DOCUMENTS

| | | | |
|---|---|---|---|
| 4,021,388 A | 3/1977 | Griffin | |
| 4,777,201 A * | 10/1988 | Shigemoto | B29C 33/68 524/269 |
| 4,823,168 A * | 4/1989 | Kamahori | G01N 21/05 250/576 |
| 5,599,503 A | 2/1997 | Manz et al. | |

(Continued)

*Primary Examiner* — Hina F Ayub
*Assistant Examiner* — Amanda Merlino
(74) *Attorney, Agent, or Firm* — Gonzales Patent Services; Ellen M. Gonzales

(57) ABSTRACT

A method using electric field assisted glass sealing (anodic bonding) to create strong, adhesive-free optical cells using a thin layer of metal between two layers of glass. The cells can be used as simple optical cells, liquid or gas flow cells, and as acousto-optical flow cells, where acoustic standing waves are used within the flow cell.

18 Claims, 3 Drawing Sheets

(56) References Cited

U.S. PATENT DOCUMENTS

2010/0128255 A1\* 5/2010 Klotzbucher ..... B01L 3/502707
356/51
2010/0192342 A1 8/2010 Ono et al.
2014/0211473 A1 7/2014 Weidman et al.

\* cited by examiner

OPTICAL CELL CONSTRUCTED BY ANODICALLY BONDING A THIN METAL LAYER BETWEEN TWO OPTICALLY CLEAR GLASS WINDOWS

CROSS-REFERENCE TO RELATED APPLICATIONS

The following application claims benefit of U.S. Provisional Application No. 62/138,192, filed Mar. 25, 2015, which is hereby incorporated by reference in its entirety.

BACKGROUND

There is a need for optical cells that can contain a liquid or gas sample for many types of optical measurements. These optical cells have been made through many methods that include complete fabrication using glass walls, quartz walls, laser cut channels in optically clear materials, and micro-fabricated cells using polymeric materials.

In addition to simple optical cells, there is also a need for flow cells that allow for fluid to be passed through the cell during optical analysis. Such flow cells can be made in similar fashion as described above.

Beyond the simple cells above (both flowing and non-flowing), it is also desirable to create optical cells that can support acoustic standing waves across one or more dimensions of the cell. Such cells must be made of materials that have a large acoustic impedance difference relative to the solution within the cell. Effectively, this means that the walls of the flow cell must be constructed from a rigid material such as glass, silicon, or a metal, all of which have a large acoustic impedance mismatch with the typical aqueous solutions used in optical measurements. Current methods of such optical cell construction have relied upon capillary devices or channels created in silicon or glass (via etching or laser cutting). Once constructed, these acoustic cells allow the particles within the cell to be manipulated using the acoustic standing wave while an optical measurement is made.

SUMMARY

The present disclosure provides a method using electric field assisted glass sealing (more commonly known as anodic bonding) to create strong, adhesive-free sealed chambers using a thin layer of metal between two layers of glass. These chambers can be used with liquid or biological samples as simple optical cells, liquid or gas flow cells, and as acousto-optical flow cells, where acoustic standing waves are used within the flow cell.

DETAILED DESCRIPTION

Figure 1:
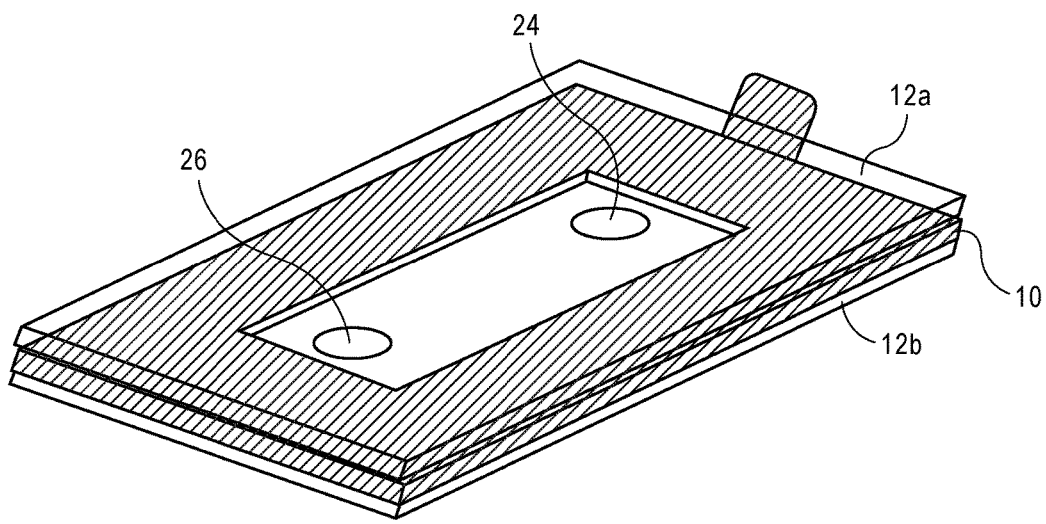
FIG. 1 is a schematic illustration of an exemplary flow cell according to an embodiment of the present disclosure.

According to an embodiment the present disclosure provides a method using electric field assisted glass sealing (more commonly known as anodic bonding) to create strong, adhesive-free sealed chambers using a thin layer of metal between two layers of glass. These chambers can be used with liquid or biological samples as simple optical cells, liquid or gas flow cells, and as acousto-optical flow cells, where acoustic standing waves are used within the flow cell.

Using anodic bonding, it is possible to bond glass, with alkali ion containing glass (e.g. soda lime float glass, Pyrex, Borofloat-33, N-BK7, etc.) being most commonly used, to a variety of electronically conductive materials, including metals and semiconductors (e.g. silicon). As anodic bonding typically requires the materials to be heated to hundreds of degrees Celsius, it is desirable that the glass and the electronically conductive material have similar coefficients of thermal expansion (CTE) to prevent fracture of the materials (usually the glass) during cooling. For that reason, most devices created using anodic bonding of a conductor to glass use CTE-matched material pairs such as 410 stainless steel and soda lime glass, silicon and Pyrex (or Borofloat-33), Kovar and N-BK7, or Super Invar and fused silica. Beyond the use of bulk metal or semiconductor substrates, it has also been shown that thin metal foils can also be anodically bonded to glass. In addition to a well-matched CTE, it is also necessary that the surfaces of the materials to be bonded be sufficiently smooth to make the intimate contact necessary for strong and reliable bonding to occur.

The present disclosure provides a method to anodically and simultaneously bond a symmetrical "sandwich" of glass/metal foil/glass. The symmetrical construction significantly relaxes the requirement for CTE matching; if the metal layer's CTE is greater than that of the outer glass layers or sheets, then the ensemble can acquire an inherently stable stress distribution upon cooling after anodic bonding. Analogous to tempered safety glass or case hardened steel, the trapped metal layer contracts more than the outer glass layers, resulting in compressive stress in the glass layers and tensile stress in the metal layer. If the yield strength of the metal layer ($YS_m$) is less than the crushing strength of the glass layers ($CS_g$), then a normal stress model may be used to estimate the ratio of the maximum allowed thickness of the metal layer $W_m(max)$ for a given thickness of the individual glass layers ($W_g$) by:

$$W_m(max)/W_g = 2(CS_g/YS_m)$$

This method eliminates the need to use CTE-matched metal layers such as Kovar or Super Invar, which are relatively expensive, difficult to machine, and less corrosion and oxidation resistant than other non-CTE-matched materials such as aluminum. Alternatively, it also eliminates the need to use monocrystalline silicon, which is prone to cleaving and brittle fracture, particularly in thin structures.

According to an embodiment, the method may be used to produce strong, adhesive-free optical cells for the analysis of liquid samples, wherein a cut-out or void in the metal layer creates a channel or fluid space for the liquid sample.

An exemplary optical cell is shown in FIG. 1. As shown, a metal layer or insert 10 is sandwiched between two glass plates 12a and 12b. The optical cell may further include one or more inlets and outlets formed in glass plate 12a, shown at 24 and 26, respectively.

Figure 2:
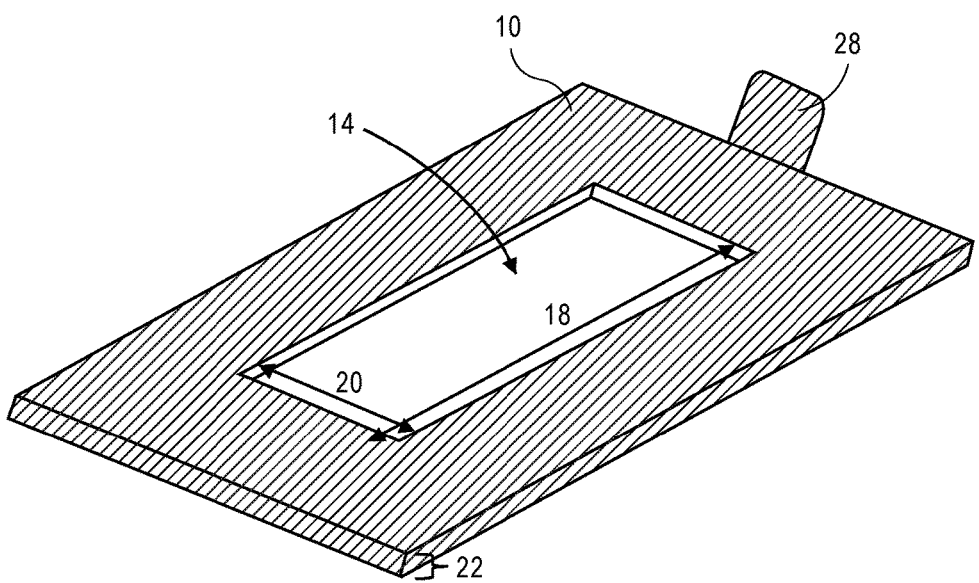
FIG. 2 is a schematic illustration of a thin metal insert for use with the flow cell of FIG. 1.

An exemplary insert, prior to sandwiching between the metal plates, is shown in FIG. 2. As shown, a void 14 in the metal insert 10 produces a channel or fluid space having the general length 18 and width 20 of the void 14 and a depth 22 equivalent to the thickness of the insert. According to some embodiments, insert 10 may include a tab 28 that can later be used, for example, to provide an electrical connection point for the anode.

Figure 3:
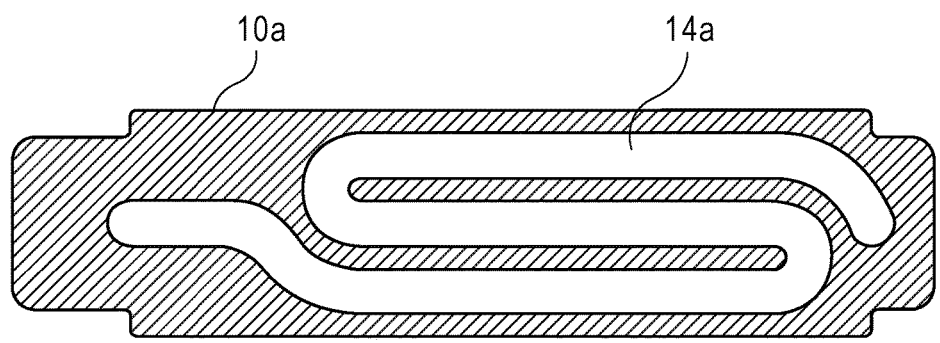
FIG. 3 is a schematic illustration of another embodiment of a thin metal insert for use with the flow cell of FIG. 1.

Of course it will be understood that void 14 may have any desirable shape or size, enabling the production of chambers/fluid cells of any desirable shape or size. It will also be understood that a single metal insert may include more than one void, resulting in more than one chamber, channel or fluid space. It will be further understood that a variety of simple or complex patterns may be formed in the metal insert enabling a near endless variety of chambers, fluid spaces, channels, etc., some or all of which may or may not be fluidly connected. Another void/channel/fluid space configurations is shown in FIG. 3, which depicts a serpentine shaped void 14a.

According to some embodiments, the void may be formed by die cutting a solid metal sheet. Alternatively, the void may be formed by a variety of process including, but not limited to die cutting, stamping, etching, electrical discharge machining, etc. Furthermore, in some embodiments the insert may be pre-manufactured to include one or more voids, i.e. via stamping, 3D printing, photolithographic patterning, etc.

The method can use a variety of metal types and thicknesses, including foils or other electrically conductive materials. Metals suitable for the present method include, but are not necessarily limited to, foils or other materials made from aluminum, stainless steel, silver, platinum as well as semiconductors such as silicon, gallium arsenide, indium phosphide, etc. According to various embodiments, the metal layer may be between 0.01 mm and 10 mm in thickness.

Suitable types of glass include, but are not limited to soda lime float glass, Pyrex, Borofloat 33, N-BK7, and fused silica.

According to a specific embodiment, the metal insert may be formed from a 0.125 mm thick commercially available aluminum foil (alloy 1100), which is inexpensive, malleable, ductile, very corrosion resistant, sufficiently oxidation resistant to allow anodic bonding in air, and relatively easy to die cut. The aluminum foil can be of standard mill-finished roughness provided by the manufacturer.

According to some embodiments, the metal layer may undergo additional processing to achieve a high degree of smoothness; generally, the surface smoothness should be less than 10 nm RMS, and preferably less than 1 nm RMS, which is typical of a moderate quality optical mirror. According to various embodiments, additional processing may include polishing, pressing or high pressure rolling. According to an embodiment, the desired degree of surface smoothness is achieved by pressing the relatively low yield strength metal layer between two smooth surfaces of a relatively high yield strength substance, such as polished flat plates of stainless steel, at very high pressures. In practice, the use of polished stainless steel plates at a pressure of 10,000 psi to press 0.125 mm thick 1100 alloy aluminum foil results in a metal insert having a very smooth, near specular, finish.

Figure 4:
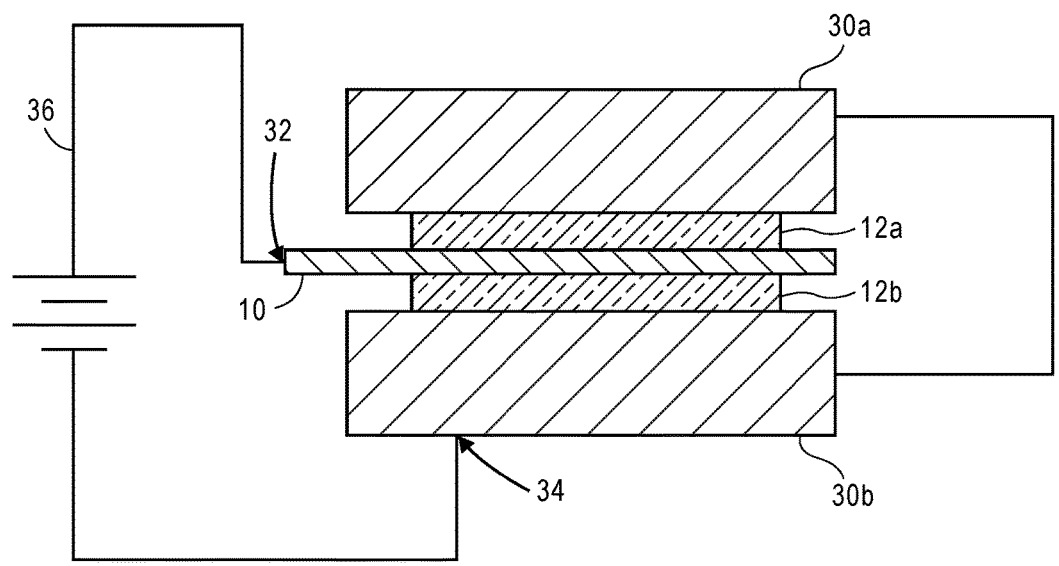
FIG. 4 is a schematic illustration of an anodic bonding machine in operation.

According to an embodiment, the smooth metal insert is placed between two glass panels and the stack is inserted into an anodic bonding apparatus. In general, to achieve anodic bonding, the stack is heated while the apparatus applies a voltage across the stack until a strong hermetic seal is produced between the glass and metal layers. Typically, suitable temperature ranges are between 150 and 500° C., while suitable voltages are between 400 and 1,200 V. Of course it will be understood that specific bonding process conditions will depend upon the choice of materials and the thickness of the layers. An exemplary anodic bonding apparatus is shown in operation in FIG. 4. As depicted, the metal insert 10 is sandwiched between glass layers 12a and 12b, which are positioned between cathodes 30a and 30b. The anode connection is shown at 32 and a cathode connection at 34. A voltage 36 is applied across the apparatus to simultaneously bond the glass and metal layers.

According to an embodiment, the methods described herein can be used to use flow cells for use with large cross-sectional aspect ratio acoustic flow cells. According to some embodiments, large aspect ratio acoustic flow cells may use a rectangular aspect ratio and multi-node acoustic standing waves to create a wide channel that has up to 64 parallel flowing sample streams to support high volumetric flow rates for particles up to several hundred microns in diameter. Accordingly, the presently described methods may be used to provide a flow cell having a channel that supports up to 10, 20, 30, 40, 50, 60, 64, or more parallel and coplanar flowing sample streams for particles up to several hundred microns in diameter.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

George. Wallis and Daniel. I. Pomerantz, "Field Assisted Glass-Metal Sealing," *Journal of Applied Physics*, Vol. 40, No. 10, September, (1969), pp. 3946-3949.
Thomas. R. Anthony, "Anodic bonding of imperfect surfaces," *Journal of Applied Physics*, Vol. 54, No. 5, May, (1983), pp. 2419-2428.
Cui-Rong Liu, Xiao-Ying Lu, Zhen-Yu Yang, Qing-Sen Meng, *International Journal of Nonlinear Sciences and Numerical Simulation*, Vol. 9, No. 4, (2008), pp. 347-353.
George W. Morey, *The Properties of Glass*, Reinhold Publishing, New York, (1945), pp. 324-325.

EXPERIMENTAL

A compressed 0.125 mm aluminum foil insert was placed between two glass slides (Schott Borofloat-33 slides; 75 mm×25 mm×1 mm). One of the glass slides had holes drilled in it to allow for fluid input and output. This stacked sandwich of glass/metal/glass was inserted into an anodic bonding apparatus that placed a large aluminum block on the top and bottom of the sandwich. The positive terminal (anode) of a high voltage power supply was attached to the tab of the thin metal layer and the negative terminal (cathode) was attached to each of the large aluminum blocks on the top and bottom of the apparatus. The entire apparatus was placed on a hot plate and heated to 300 degrees Celsius. At this point, the power supply was used to apply a 1000V field across the sandwich for a period of several hours, including the cooling period. This resulted in a strong hermetic seal of both glass layers to the thin metal layer. The holes in the top slide were used to attach fluidic connections. In the given example, the void in the thin metal layer was 8 mm wide and 65 mm long, which created a 0.125 mm high by 8 mm wide by 65 mm long flow channel in an optical cell. This device was created (FIG. 5) and tested for leaks using water. Water was driven by a syringe at approximately 60 mL/min through the flow cell without any leaks whatsoever. This cell is optically clear, water tight, and supports high fluid flow rates. The top and bottom of the cell are made from high quality optical grade glass.

To evaluate the ability of these optical flow cells to support acoustic standing waves for particle manipulation, commercially available piezoelectric transducer acoustic drives made of lead zirconate titanate (PZT) were attached to the device. The pictured flow cell shows a PZT piezo ceramic acoustic driver attached to the glass slide. Another PZT is attached to the other glass slide to serve as an acoustic pickup.

Figure 5:
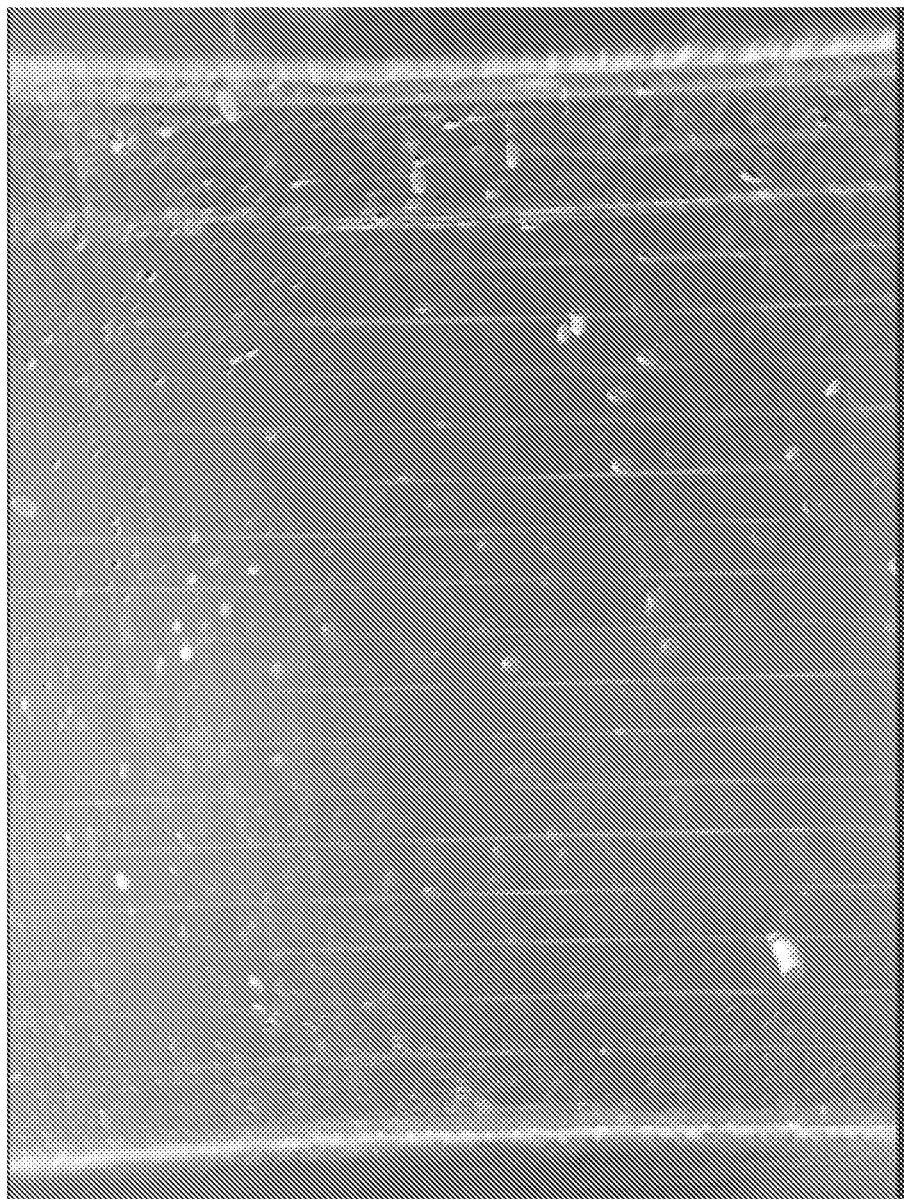
FIG. 5 shows the particles streams that are created by acoustic manipulation of the particles within the optical flow cell.

The optical flow cell was attached to an amplified function generator and the PZT was driven with an acoustic sine wave at 1.733 MHz with a drive voltage of ~40V peak to peak. This is predicted to create 19 acoustic pressure nodes within the system. The effectiveness of this system in supporting acoustic manipulation was shown when we flowed 8 μm diameter polystyrene particles in water at 20 mL/min to generate the expected 19 nodes, where the flowing particles were focused by the acoustic standing wave. FIG. 5 shows the particles streams that are created by acoustic manipulation of the particles within the optical flow cell. This clearly demonstrates that the optical cell can support acoustic standing waves.

What is claimed is:

1. A device comprising:
    a metal insert comprising a void simultaneously anodically bonded between two plates of glass wherein combined edges of the void and glass plates form a sealed chamber wherein at least one of the glass plates further includes a hole that is fluidly connected to the sealed chamber so as to form an inlet to or outlet from the chamber.

2. The device of claim 1 wherein at least one of the glass plates further includes a second hole that is fluidly connected to the sealed chamber so as to form an inlet to or outlet from the chamber.

3. The device of claim 1 wherein the metal insert is formed from a metal foil.

4. The device of claim 1 wherein the metal is aluminum.

5. The device of claim 1 wherein the metal insert has a thickness between 0.01 mm and 10 mm.

6. The device of claim 1 wherein the metal insert has a smoothness of less than 10 nm RMS.

7. The device of claim 1 wherein the metal insert has a smoothness of less than 1 nm RMS.

8. The device of claim 1 wherein the void is rectangular.

9. The device of claim 1 wherein the void is serpentine-shaped.

10. The device of claim 1 wherein the glass and metal have unmatched coefficients of thermal expansion.

11. A method for forming a sealed chamber comprising:
    providing a metal insert comprising a void;
    sandwiching the metal insert between two glass plates; and
    simultaneously anodically bonding the metal insert to the glass plates to form the sealed chamber wherein at least one of the glass plates has a hole that, when the insert is positioned between the glass plates, is fluidly connected to the void so as to form an inlet to or outlet from the chamber.

12. The method of claim 11 wherein the metal insert has a thickness between 0.01 mm and 10 mm.

13. The method of claim 11 wherein the metal insert is formed from a metal foil.

14. The method of claim 13 wherein the metal insert has a smooth finish.

15. The method of claim 14 wherein the metal insert has a smoothness of less than 10 nm RMS.

16. The method of claim 15 wherein the metal insert has a smoothness of less than 1 nm RMS.

17. The method of claim 11 wherein the smooth finish is obtained by pressing the relatively low yield strength metal foil insert between polished plates of relatively high yield strength material.

18. The method of claim 11 wherein the glass and metal have unmatched coefficients of thermal expansion.

* * * * *